US011419906B2

United States Patent
Majeed et al.

(10) Patent No.: US 11,419,906 B2
(45) Date of Patent: Aug. 23, 2022

(54) METHOD AND COMPOSITION FOR THERAPEUTIC MANAGEMENT OF GLUTEN INTOLERANCE

(71) Applicants: Muhammed Majeed, Bangalore (IN); Kalyanam Nagabhushanam, East Windsor, NJ (US); Kirankumar Beede, Bangalore (IN); Sivakumar Arumugam, Bangalore (IN); Shaheen Majeed, Springville, UT (US)

(72) Inventors: Muhammed Majeed, Bangalore (IN); Kalyanam Nagabhushanam, East Windsor, NJ (US); Kirankumar Beede, Bangalore (IN); Sivakumar Arumugam, Bangalore (IN); Shaheen Majeed, Springville, UT (US)

(73) Assignee: SAMI-SABINSA GROUP LIMITED, Bangalore (IN)

( * ) Notice: Subject to any disclaimer, the term of this patent is extended or adjusted under 35 U.S.C. 154(b) by 148 days.

(21) Appl. No.: 16/836,066

(22) Filed: Mar. 31, 2020

(65) Prior Publication Data
US 2020/0316140 A1    Oct. 8, 2020

Related U.S. Application Data

(60) Provisional application No. 62/827,955, filed on Apr. 2, 2019.

(51) Int. Cl.
*A61K 35/742*    (2015.01)
*A61K 38/46*     (2006.01)
*A61K 38/47*     (2006.01)

(52) U.S. Cl.
CPC .......... *A61K 35/742* (2013.01); *A61K 38/465* (2013.01); *A61K 38/47* (2013.01); *C12Y 301/01003* (2013.01); *C12Y 302/01001* (2013.01); *C12Y 302/01004* (2013.01); *C12Y 302/01108* (2013.01)

(58) Field of Classification Search
CPC .... A61K 35/742; A61K 38/465; A61K 38/47; A61K 38/54; C12Y 301/01003; C12Y 302/01001; C12Y 302/01004; C12Y 302/01108
See application file for complete search history.

(56) References Cited

U.S. PATENT DOCUMENTS 7,767,203 B2 * 8/2010 Farmer ................ A61P 1/12
424/93.46

OTHER PUBLICATIONS

Makharia A, Catassi C, Makharia GK. The Overlap between Irritable Bowel Syndrome and Non-Celiac Gluten Sensitivity: A Clinical Dilemma. Nutrients. 2015;7(12):10417-10426. Published Dec. 10, 2015. doi:10.3390/nu7125541.*
Majeed M, Nagabhushanam K, Natarajan S, Sivakumar A, Ali F, Pande A, Majeed S, Karri SK. Bacillus coagulans MTCC 5856 supplementation in the management of diarrhea predominant Irritable Bowel Syndrome: a double blind randomized placebo controlled pilot clinical study. Nutr J. Feb. 27, 2016;15:21. doi: 10.1186/S12937.*
"Ultra Probiotic", ncweight.com/products/bi-prozyme, North Carolina Weight and Wellness website available online on Nov. 14, 2016, retrieved on Jan. 26, 2022, 2 pages of PDF.*
Shikham, A. K. "Role of Probiotics in Improving Gut Health in Celiac Disease", Celiac.com website, 2014, 6 pages of PDF retrieved on Jan. 26, 2022.*

* cited by examiner

*Primary Examiner* — Kade Ariani

(57) ABSTRACT

The present invention discloses the potential of probiotic bacteria *Bacillus coagulans* individually or in combination with multi-enzyme complex for reducing gluten content in foods rich in gluten and for the increased utilization of gluten. The invention further discloses a method for the management of gluten intolerance using composition comprising *Bacillus coagulans* and multi-enzyme complex in mammals.

6 Claims, 3 Drawing Sheets

METHOD AND COMPOSITION FOR THERAPEUTIC MANAGEMENT OF GLUTEN INTOLERANCE

CROSS-REFERENCE TO RELATED APPLICATIONS

This application is a non-provisional filing of U.S. provisional application No. 62/827,955, filed on 2 Apr. 2019.

BACKGROUND OF THE INVENTION

Field of the Invention

The invention in general relates to probiotic compositions. More specifically, the present invention relates to a composition comprising *Bacillus coagulans* individually and/or in combination with multi-enzyme complex for the enhancing utilization of gluten and in the therapeutic management of gluten intolerance.

Description of Prior Art

Gluten is a protein that originates in cereal grains, such as wheat, rye and barley. Role of gluten in wheat is to improve water absorption capacity, viscosity, elasticity of dough. There are two types in gluten proteins viz. gliadin, which is insoluble in water and the soluble glutenin. The gliadin fraction of wheat has been traditionally considered toxic specifically is people with coeliac disease. Coeliac disease is an autoimmune-mediated intestinal disorder induced by prolamins present in wheat (gliadin), rye (secalin) and barley (hordein), and belongs to the most common food-related disorders in western countries. The disease has a strong genetic component (human leucocyte antigen DQ2 or DQ8) and is characterized by small-intestinal villous atrophy, crypt hyperplasia and a profound immune response in the mucosa. Children with gluten intolerance have lot of effects including failure to thrive in infants, delayed puberty in adolescents, irritability in mood, short stature, and dental enamel defects. Gluten free diet has been reported to be an effective treatment strategy for managing gluten intolerance and related conditions like Celiac disease (Niewinski M M, Advances in Celiac Disease and Gluten-Free Diet, J Am Diet Assoc. 2008;108:661-672). Thus, it is imperative to reduce the gluten content in foods and increase gluten utilization to decrease the toxic effects of gluten.

Effective diet control measures for people with coeliac disease is to remove gluten from diet. Several research lines are concentrated in developing novel forms of therapy for coeliac disease. These include detoxification of the disease-driving gluten and gliadin peptides as well as blockage of the gluten-induced inflammatory response. Supplementation of digestive enzymes can be an effective therapy for the degradation of gluten. In another approach gluten detoxification can also be done during food processing by fermentation using probiotics and administering probiotics to enhance gluten utilization by the probiotic bacteria.

The use of probiotics for the management of gluten intolerance is already reported in literature. The following articles are incorporated herein by reference.

1. Samsel A, Seneff S, Glyphosate, pathways to modern diseases II: Celiac sprue and gluten intolerance. Interdiscip Toxicol. 2013 6(4): 159-84. doi: 10.2478/intox-2013-0026.
2. De Angelis M, Rizzello C G, Fasano A, Clemente M G, De Simone C, Silano M, De Vincenzi M, Losito I, Gobbetti M. VSL #3 probiotic preparation has the capacity to hydrolyze gliadin polypeptides responsible for Celiac Sprue. Biochim Biophys Acta 1762(1):80-93. Epub 2005 Oct. 21.
3. Wei G, Tian N, Siezen R, Schuppan D, Helmerhorst E J (2016) Identification of food-grade subtilism's as gluten-degrading enzymes to treat celiac disease. Am J Physiol Gastrointest Liver Physiol 311(3): G571-G580.

The use of digestive enzymes for the management of gluten intolerance and increase utilisation of gluten is also known (Ido et. al., Combination of Gluten-Digesting Enzymes Improved Symptoms of Non-Celiac Gluten Sensitivity: A Randomized Single-blind, Placebo-controlled Crossover Study, Clin Transl Gastroenterol. 2018 Sep: 9(9): 181.

However, it is well known in the scientific art that biological effects of probiotics or products thereof are strain specific and cannot be generalised among genera, species and strains (Probiotics: In Depth/NCCIH, U.S. Department of Health and Human Services, National Institutes of Health—incorporated herein by reference). Hence, there exists a need to find a superior probiotic strain with improved gluten utilisation and removal potential. The present invention solves the above problem by disclosing the therapeutic potential of probiotic bacteria *Bacillus coagulans* MTCC 5856 for the management of gluten intolerance and increased removal of gluten from food stuff. The invention also discloses a synergistic combination comprising probiotic bacteria *Bacillus coagulans* and multi-enzyme complex for above use.

It is the principle object of the invention to disclose the use of probiotic bacteria *Bacillus coagulans* individually or in combination with multi-enzyme complex for removing gluten content in food.

It is another objective of the invention to disclose the use of probiotic bacteria *Bacillus coagulans* individually or in combination with multi-enzyme complex for the enhancing gluten utilization in mammals.

It is yet another objective of the invention to disclose the use of probiotic bacteria *Bacillus coagulans* individually or in combination with multi-enzyme complex for the therapeutic management of gluten intolerance and related conditions in mammals The present invention solves the above mentioned objectives and provides further related advantages.

DEPOSIT OF BIOLOGICAL MATERIAL

The deposit of biological material *Bacillus coagulans* bearing accession number MTCC 5856, mentioned in the instant application has been made on 19 Sep. 2013 at Microbial Type Culture Collection & Gene Bank (MTCC), CSIR-Institute of Microbial Technology, Sector 39-A, Chandigarh-160036, India.

SUMMARY OF THE INVENTION

The present invention discloses the potential of probiotic bacteria *Bacillus coagulans* individually or in combination with multi-enzyme complex for reducing gluten content in food rich in gluten.

The invention further discloses the potential probiotic bacteria *Bacillus coagulans* individually or in combination with multi-enzyme complex for increased utilization of gluten in mammals.

The invention further discloses a method for the management of gluten intolerance and related conditions using a composition comprising *Bacillus coagulans* and multi-enzyme complex.

Other features and advantages of the present invention will become apparent from the following more detailed description, which illustrate, by way of example, the principle of the invention.

DESCRIPTION OF THE PREFERRED EMBODIMENTS

Figure 1:
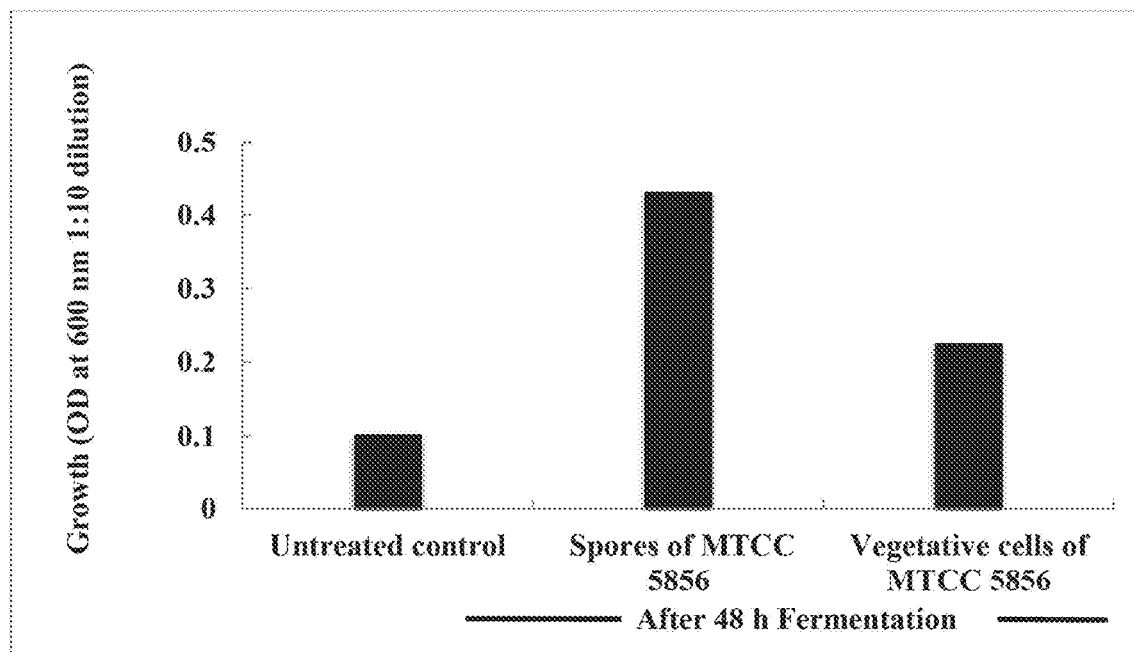
FIG. 1 shows the graphical representation of growth of *Bacillus coagulans* MTCC 5856 spores and vegetative cells in media containing gluten.

In the most preferred embodiment, present invention relates to a method of reducing gluten content in foods, said method comprising step of bringing into contact foods containing gluten with probiotic bacteria *Bacillus coagulans* individually or in combination with multi enzyme complex to bring about the effect of reducing gluten content. In a related embodiment, the type of gluten is selected from the group comprising, Gliadin, Hordeins, Avenins, and Secalins. In another related embodiment, the foods containing true gluten is barley, wheat, rye, and oats. In another related embodiment, the foods containing gluten is selected from but not limited to glutens in flours of Barley, Wheat, Rye, and Oats. In another related embodiment, the foods containing gluten is selected from but not limited to wheat, all purpose flour, almond flour, rice flour, corn flour, graham flour, semolina, Farro flour. In another related embodiment, the gluten from wheat is selected from different types of wheat species mainly Farro medio or Emmer wheat, Farro piccolo or Einkom wheat, Farro grande or Spelt wheat, triticale, durum, khorsan, kamut. In a related embodiment, *Bacillus coagulans* strain is specifically MTCC 5856. In yet another related embodiment, the effective dose of *Bacillus coagulans* is $2\times10^9$ colony forming units (cfu). In yet another related embodiment, the multi-enzyme complex comprises of a) α-amylase: not less than 24000 DU/g, b) cellulase: not less than 1100 CU/g, c) lipase: not less than 200 FIP/g, d) lactase: not less than 4000 ALU/g and e) neutral or acid protease: not less than 6000 PC/g.

In another most preferred embodiment, invention relates to a method of increasing gluten utilization in mammals, said method comprising step of administering probiotic bacteria *Bacillus coagulans* individually and/or in combination with multi-enzyme complex to said mammals to bring about an effect of increased utilization of gluten. In a related embodiment, *Bacillus coagulans* strain is specifically MTCC 5856. In yet another related embodiment, the effective dose of *Bacillus coagulans* is $2\times10^9$ colony forming units (cfu). In yet another related embodiment, the multi-enzyme complex comprises of a) α-amylase: not less than 24000 DU/g, b) cellulase: not less than 1100 CU/g, c) lipase: not less than 200 FIP/g, d) lactase: not less than 4000 ALU/g and e) neutral or acid protease: not less than 6000 PC/g. In another related embodiment, the mammal is human.

In yet another most preferred embodiment, invention relates to a method for the therapeutic management of gluten intolerance and related conditions in mammals by enhancing gluten utilization, said method comprising step of administering a composition comprising probiotic bacteria *Bacillus coagulans* individually or in combination with multi-enzyme complex to mammals in need of such therapy, to bring about a reduction is symptoms of gluten intolerance. In related embodiment, *Bacillus coagulans* strain is specifically MTCC 5856. In yet another related embodiment, the effective dose of *Bacillus coagulans* is $2\times10^9$ colony forming units (cfu). In yet another related embodiment, the multi-enzyme complex comprises of a) α-amylase: not less than 24000 DU/g, b) cellulase: not less than 1100 CU/g, c) lipase: not less than 200 FIP/g, d) lactase: not less than 4000 ALU/g and e) neutral or acid protease: not less than 6000 PC/g. In yet another related embodiment, the symptoms of gluten intolerance are selected from the group comprising, but not limited to, chronic diarrhea, bloated stomach, stomach cramps and pains, joint pain, canker sores inside mouth, missed menstrual periods, headache, anemia, fatigue, depression and anxiety, nausea and vomiting, nasal congestion, difficulty breathing or anaphylaxis, eye irritation, hives and rash, abdominal bloating and gas, constipation, pale and foul-smelling stool. In another related embodiment, related conditions of gluten intolerance are selected from the group consisting of autoimmune disorders like celiac disease, dermatitis herpetiformis, gluten ataxia, non-celiac gluten sensitivity (NCGS), gluten ingestion, Gluten mal-absorption. In another related embodiment, composition comprising *Bacillus coagulans* alone or in combination with multi-enzyme complex is formulated with pharmaceutically/nutraceutically acceptable excipients, adjuvants, bases, diluents, carriers, conditioning agents, bioavailability enhancers, antioxidants and preservatives and administered orally in form of tablets, capsules, syrups, gummies, powders, suspensions, emulsions, chewables, candies or eatables.

The specific examples included herein below illustrate the aforesaid most preferred embodiments of the present invention.

EXAMPLE 1

Utilization of Gluten (GL) by *Bacillus Coagulans* MTCC 5856 in Media

Methodology

*B. coagulans* MTCC 5856 was grown in media (Compositions: 5 g/l Peptic digest of animal tissue, 5 g/l Yeast extract, 2 g/l Dextrose, 0.5 g/l Dipotassium phosphate, 0.5 g/l Monopotassium phosphate, 0.3 g/l Magnesium sulfate and 0.3 g/l sodium chloride, 0.1 g/l Manganese sulphate pH 6.5). After 48 h of incubation, a seed of 250 ml was washed with saline twice and final pallet was added with 10 ml of saline and transferred to fresh sterile media.

After 24 h of incubation, the seed was transferred to fresh sterile media (Composition: 2.5 to 10 g/l gluten from wheat (sigma-Aldrich), 2.5 g/l Dextrose, 1.0 g/l Dipotassium phosphate, 1.0 g/l Monopotassium phosphate, 0.5 g/l Magnesium sulfate and 2 g/l sodium chloride, pH 6.5) and incubated at 37° C. for 72 h with 180 rpm. After every 24, 48 and 72 h of incubation, the fermented broth was collected and freeze dried (VirTis 2 K Freeze Dryer, SP Industries, Inc., Warminster, Pa. USA). Further, the powder was collected and gliadin content analysis carried out using Veratox® for Gliadin R5 kit. The assays were performed according to the manufacturers' instructions as described.

Veratox for Gliadin R5 is a sandwich enzyme-linked immunosorbent assay (S-ELISA). Gliadin is extracted from samples with a 60% ethanol solution by shaking in a shaker. Added 150 µL controls and extracted samples to transfer wells. Then, transferred 100 µL to the antibody wells and incubated for 10 minutes and mixed for 20 seconds by sliding back and forth on a flat surface and dump liquid from antibody wells. Transferred 100 µL conjugate from reagent boat to antibody wells using 12-channel pipe tier, mixed for 20 seconds by sliding back and forth on a flat surface and incubated for 10 minutes. After incubation, the solution was added with 100 µL substrate from reagent boat to antibody wells using 12-channel pipettor and incubated for 10 minutes. Mixed well for 20 seconds by sliding back and forth on a flat surface. Further, transferred 100 µL red Stop from reagent boat to antibody wells and mixed well and read results in a microwell reader. The development of blue color indicates that the samples contain high levels of gliadin while purple or red samples contain little or no gliadin. The optical densities of the controls form a standard curve, and the sample optical densities are plotted against the curve to calculate the exact concentration of gliadin in parts per million (ppm).

Results

Data of the study suggested that *Bacillus coagulans* MTCC 5856 has ability to grow while fermenting Wheat gluten as nutritional source (FIG. 1)

Figure 2:
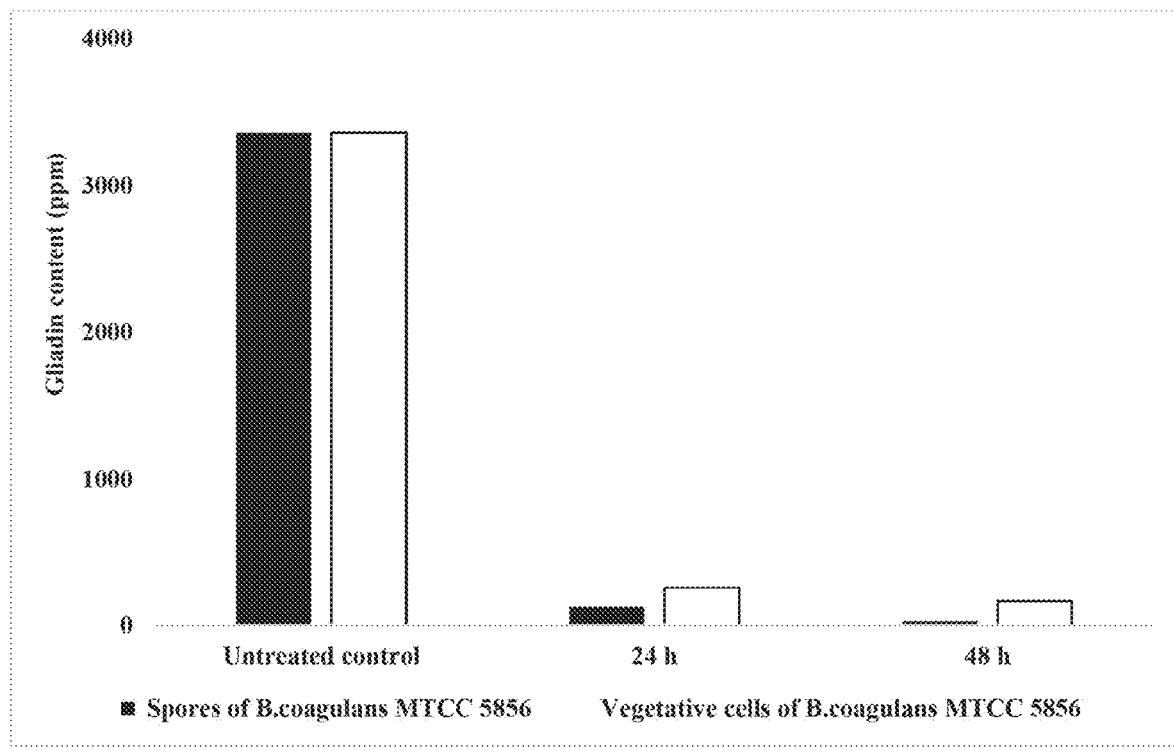
FIG. 2 shows the graphical representation of *Bacillus coagulans* MTCC 5856 showing the ability to reduce gluten content in the media.

With regard to the potential of *Bacillus coagulans* to remove gliadin content, both the spores and vegetative cells of *Bacillus coagulans* MTCC 5856 significantly removed the gliadin content from the media (FIG. 2)

EXAMPLE 2

Utilization of Gluten by *Bacillus Coagulans* MTCC 5856 in Wheat Flour (WF)

Methodology

*B. coagulans* MTCC 5856 was grown in media (Composition: 5 g/l Peptic digest of animal tissue, 5 g/l Yeast extract, 2 g/l Dextrose, 0.5 g/l Dipotassium phosphate, 0.5 g/l Monopotassium phosphate, 0.3 g/l Magnesium sulfate and 0.3 g/l sodium chloride, 0.1 g/l Manganese sulphate pH 6.5 ). After 48 h of incubation, seed of 250 ml was washed with saline twice and final pallet was mixed with 10 ml of saline and transferred to fresh sterile media.

After 24 h of incubation, seed was transferred to fresh sterile media (Composition: 2.5 to 10 g/l wheat flour in 1000 ml of Potassium phosphate buffer (0.1 M, pH 6.5) and incubated at 37° C. for 72 h with 180 rpm. After every 24, 48 and 72 h of incubation, the fermented broth was collected and freeze dried. Further, the powder was collected and carried out gliadin content analysis using Veratox® for Gliadin R5 kit as per the procedure described in example 1.

Results

Figure 3:
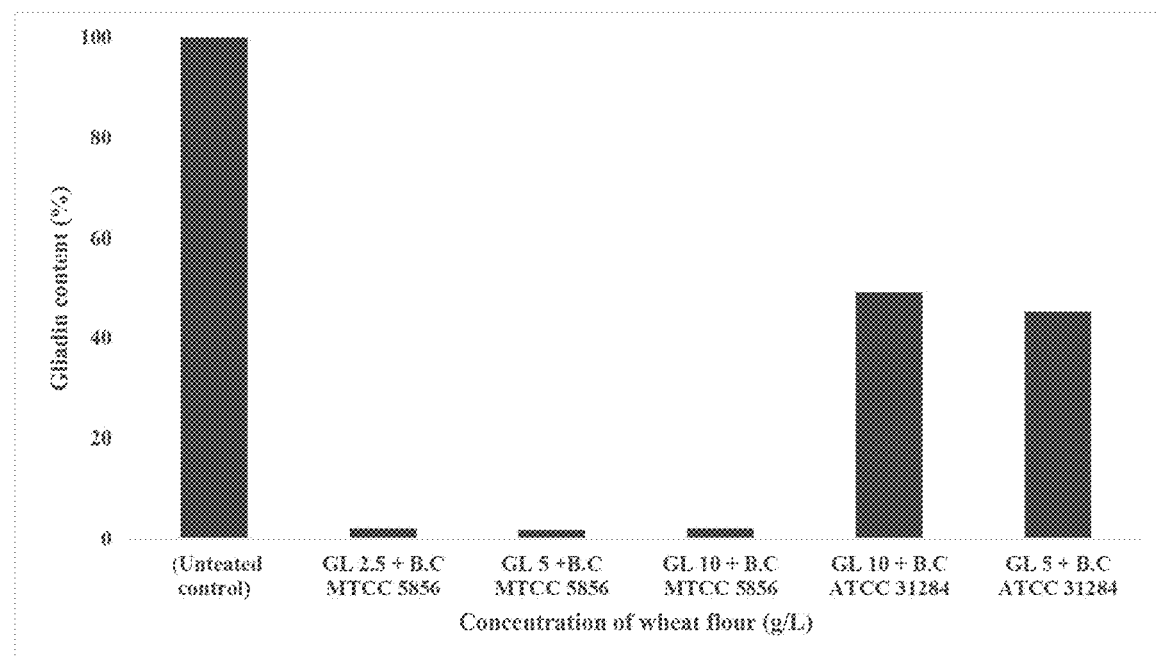
FIG. 3 shows the graphical representation of reduction in gliadin content from wheat flour (WF) by *Bacillus coagulans* MTCC 5856

Spores and vegetative cells of *Bacillus coagulans* MTCC 5856 were incubated with whole wheat flour. Both spores and vegetative cells of *Bacillus coagulans* MTCC 5856 significantly removed the gliadin content from the wheat flour. (FIG. 3)

Further, the ability of *Bacillus coagulans* MTCC 5856 to remove the gliadin content from wheat was compared with other strains was *Bacillus coagulans* (*Bacillus coagulans* ATCC 31284). *Bacillus coagulans* MTCC 5856 was much more effective in removing the gliadin content from wheat compared to *Bacillus coagulans* ATCC 31284 (Table 1).

TABLE 1

Comparison of reduction of gliadin content (ppm) from wheat flour (WF) by *B.coagulans* MTCC 5856 and *B.coagulans* ATCC 31284

| Gliadin content in Wheat flour Untreated (ppm) | Gliadin content in Wheat flour with *B.coagulans* MTCC 5856 (ppm) | Gliadin content in Wheat flour with *B.coagulans* ATCC 31284 (ppm) |
| --- | --- | --- |
| 929 | 29.84 | ND |
| 2457 | 19.58 | 1102 |
| 4685 | 11.57 | 2315 |

ND—Not done

Figure 4:
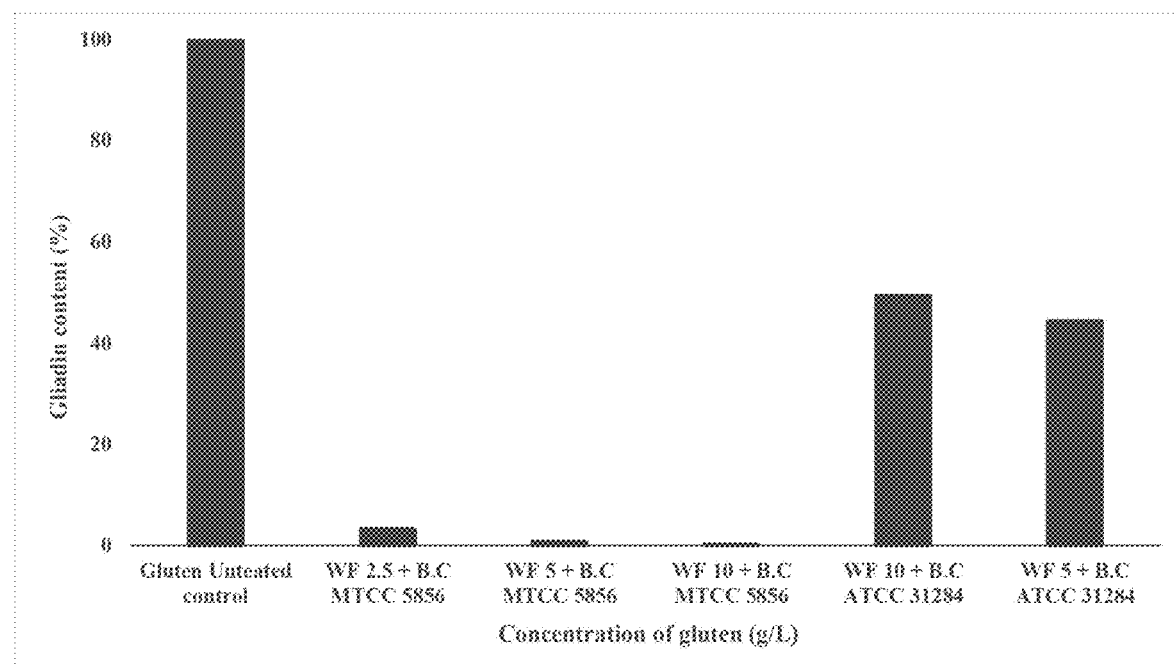
FIG. 4 shows the graphical representation of reduction in gliadin content from wheat gluten by *Bacillus coagulans* MTCC 5856

Similarly, *B. coagulans* MTCC 5856 was much effective in removing the gliadin content from wheat gluten (FIG. 4 and table 2) compared to *B. coagulans* ATCC 31284.

TABLE 2

Comparison of reduction of gliadin content (ppm) from wheat gluten (WG) by *B.coagulans* MTCC 5856 and *B.coagulans* ATCC 31284

| Gluten Untreated (ppm) | Gluten with *B.coagulans* MTCC 5856 (ppm) | Gluten with *B.coagulans* ATCC 31284 (ppm) |
| --- | --- | --- |
| 586 | 12.45 | ND |
| 1914 | 35.24 | 906 |
| 3681 | 78.6 | 1912 |

ND—Not done

EXAMPLE 3

Combination Study of *Bacillus Coagulans* MTCC 5856 and Multi-Enzyme Complex for the Utilization of Gluten (GL) in Media and in Wheat Flour (WT)

*B. coagulans* MTCC 5856 was grown in media (Compositions: 10 g/l gluten from wheat (sigma-Aldrich), 2.5 g/l Dextrose, 1.0 g/l Dipotassium phosphate, 1.0 g/l Monopotassium phosphate, 0.5 g/l Magnesium sulfate and 2 g/l sodium chloride, pH 6.5) and various concentrations of multi-enzyme complex (150 mg/L) were added after the media sterilization and along with *B. coagulans* MTCC 5856 and incubated at 37° C. for 72 h. After 72 h of incubation, the fermented broth was collected and freeze dried (VirTis 2 K Freeze Dryer, SP Industries, Inc., Warminster, Pa. USA). Further, the powder was collected and carried out gliadin content analysis. One group without multi-enzyme complex was also taken in this experiment. The contents of the multi-enzyme complex is disclosed in table 3.

TABLE 3

Composition of the multi-enzyme complex (MEC)

| Sr. No. | Enzyme | Activity (Unit/g) |
|---|---|---|
| 1 | α-Amylase | 24000 DU |
| 2 | Neutral Protease | 6000 PC |
| 3 | Cellulase | 1100 CU |
| 4 | Lactase | 4000 ALU |
| 5 | Lipase | 200 FIP |

DU, Dextrinizing Unit;
PU, Protease Unit;
CU, Cellulase Unit;
ALU, Acid Lactase Unit;
FIP, Federation Internationale de Pharmaceutiques Unit Another experiment was performed using media containing Composition: 10 g/l wheat flour in 1000 ml of Potassium phosphate buffer (0.1 M, pH 6.5) and incubated at 37° C. for 72 h with 180 rpm. After every 24, 48 and 72 h of incubation, the fermented broth was collected and freeze dried. Further, the powder was collected and carried out gliadin content analysis and multi enzyme complex (150 mg/L) were added after the media sterilization and along with B. coagulans MTCC 5856 and incubated at 37° C. for 72 h. After 72 h of incubation, the fermented broth was collected and freeze dried. Further, the powder was collected and carried out gliadin content analysis. One group without multi-enzyme complex was also taken in this experiment.

Results

The results are given in Table 4.

TABLE 4

Reduction of gliadin content from wheat flour and wheat gluten by B. coagulans MTCC 5856 and MEC (Multi enzyme complex)

| Composition | Gliadin content (ppm) |
|---|---|
| Wheat Gluten 10 g/L (Untreated control) | 3678 |
| Wheat Gluten 10 g/L + MEC 150 mg | 860 |
| Wheat Gluten 10 g/L + MEC 150 mg + B. coagulans 5856 | 3.78 |
| Wheat flour 10 g/L (Untreated control) | 4671 |
| Wheat flour 10 g/L + MEC 150 mg | 855 |
| Wheat flour 10 g/L + MEC 150 mg + B. coagulans 5856 | 4.04 |

Figure 5:
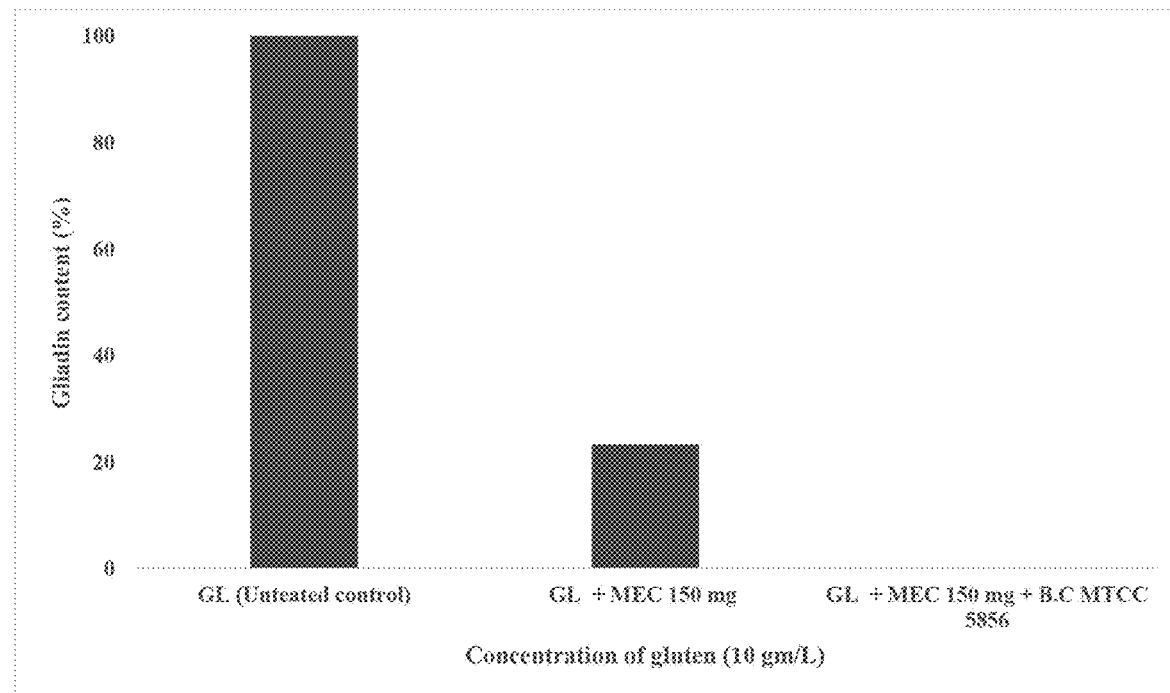
FIG. 5 shows the graphical representation of reduction in gliadin content from wheat gluten by *Bacillus coagulans* MTCC 5856 and MEC (Multi enzyme complex)
Figure 6:
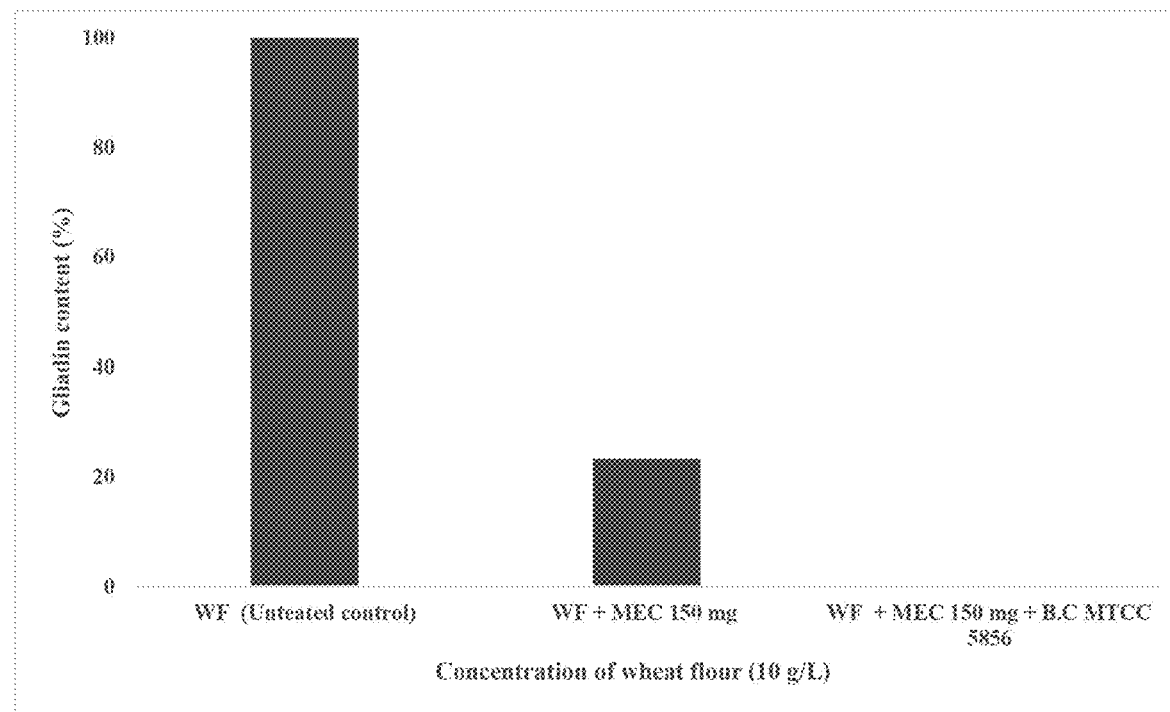
FIG. 6 shows the graphical representation of reduction in gliadin content from wheat floor by *Bacillus coagulans* MTCC 5856 and MEC (Multi enzyme complex)

The combination of B. coagulans and multi-enzyme complex shows synergistic effect on lowering the gliadin content in both whole wheat grains and wheat flour as compared to multi enzyme complex individually as shown in Table 4 and FIG. 5 & FIG. 6.

EXAMPLE 4

Formulations Containing Bacillus Coagulans and Multi-Enzyme Complex for Lactose Intolerance Bacillus coagulans and multi-enzyme complex is formulated with pharmaceutically/nutraceutically acceptable compositions with excipients, adjuvants, bases, diluents, carriers, conditioning agents, bioavailability enhancers, antioxidants and preservatives and/or combined with other hepatoprotective compositions and administered orally in form of tablets, capsules, syrups, gummies, powders, suspensions, emulsions, chewables, candies or eatables and administered for treatment gluten intolerance. The following tables provide examples of different Bacillus coagulans and multi-enzyme complex compositions.

Tables 5-10 Provide illustrative examples of formulations containing Bacillus coagulans MTCC 5856 (LACTOSORE®) for the treatment/management of gluten intolerance.

TABLE 5

Bacillus coagulans tablet

Active Ingredients

Bacillus coagulans MTCC 5856; 2 billion cfu (LACTOSORE®)
Excipients

Microscystalline cellulose, Colloidal Silica, Magnesium Stearate

* ®-Registered trade mark of Sabinsa Corporation, USA

TABLE 6

Bacillus coagulans capsule

Active Ingredients

Bacillus coagulans MTCC 5856; 2 billion cfu (LACTOSORE®)
Excipients

Maltodextrin

* ®-Registered trade mark of Sabinsa Corporation, USA

TABLE 7

Bacillus coagulans drink mix

Active Ingredients

Bacillus coagulans MTCC 5856; 2 billion cfu (LACTOSORE®)
Excipients

Maltodextrin, Taurin, Citric acid, Sucralose, Flavouring agent, Vitamin B6 and B12

* ®-Registered trade mark of Sabinsa Corporation, USA

TABLE 8

Bacillus coagulans + multi-enzyme complex (DigeZyme®) tablet

Active Ingredients

Bacillus coagulans MTCC 5856; 2 billion cfu (LACTOSORE®)
Multi-enzyme complex (DigeZyme®)
Excipients Microscystalline cellulose, Colloidal Silica, Magnesium Stearate

* ®-Registered trade mark of Sabinsa Corporation, USA

TABLE 9

Bacillus coagulans + multi-enzyme complex (DigeZyme®) drink mix

Active Ingredients

Bacillus coagulans MTCC 5856; 2 billion cfu (LACTOSORE®)
Multi-enzyme complex (DigeZyme®)
Excipients Maltodextrin, Taurin, Citric acid, Sucralose, Flavouring agent, Vitamin B6 and B12

* ®-Registered trade mark of Sabinsa Corporation, USA

TABLE 10

Bacillus coagulans + multi-enzyme complex (DigeZyme ®) capsule

Active Ingredients

Bacillus coagulans MTCC 5856; 2 billion cfu (LACTOSORE ®)
Multi-enzyme complex (DigeZyme ®)
Excipients Maltodextrin

* ®-Registered trade mark of Sabinsa Corporation, USA

The above formulations are merely illustrative examples; any formulation containing the above active ingredient intended for the said purpose will be considered equivalent.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention. The scope of the invention is to be interpreted only in conjunction with the appended claims.

We claim:

1. A method for the therapeutic management of gluten intolerance and related conditions in mammals by enhancing gluten utilization, said method. comprising step of administering a composition comprising an effective dose of probiotic bacteria *Bacillus coagulans* MTCC 5856 individually or in combination with multi-enzyme complex to mammals in need of such therapy to bring about a reduction is symptoms of gluten intolerance.

2. The method as in claim 1, wherein the effective dose of *Bacillus coagulans* MTCC 5856 is $2 \times 10^9$ colony forming units (cfu).

3. The method as in claim 1, wherein the probiotic bacteria *Bacillus coagulans* MTCC 5856 is in combination with the multi-enzyme complex comprises of a) α-amylase: not less than 24000 U/g, b) cellulase: not less than 1100 CU/g, c) lipase: not less than 200 FIP/g, d) lactase: not less than 4000 ALU/g and e) neutral or acid protease: not less than 6000 PC/g.

4. The method as in claim 1, wherein the related conditions of gluten intolerance are selected from the group consisting of celiac disease, dermatitis herpetiformis, gluten ataxia, non-celiac gluten sensitivity (NCGS), gluten ingestion, Gluten malabsorption.

5. The method as in claim 1, wherein the mammal is human.

6. The method as in claim 1, wherein the composition comprising *Bacillus coagulans* MTCC 5856 individually or in combination with multi-enzyme complex is formulated with pharmaceutically/nutraceutically acceptable excipients, adjuvants, bases, diluents, carriers, conditioning agents, bioavailability enhancers, antioxidants and preservatives and is an orally administered composition in form of tablets, capsules, syrups, gummies, powders, suspensions, emulsions, chewables, candies or eatables.

* * * * *